United States Patent
Biber

(10) Patent No.: US 10,188,313 B2
(45) Date of Patent: Jan. 29, 2019

(54) MAGNETIC RESONANCE IMAGING APPARATUS AND METHOD FOR MEASUREMENT SIGNAL ACQUISITION IN A MAGNETIC RESONANCE IMAGING APPARATUS

(71) Applicant: Stephan Biber, Erlangen (DE)

(72) Inventor: Stephan Biber, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 922 days.

(21) Appl. No.: 14/619,300

(22) Filed: Feb. 11, 2015

(65) Prior Publication Data

US 2015/0244482 A1    Aug. 27, 2015

(30) Foreign Application Priority Data

Feb. 26, 2014    (DE) .................. 10 2014 203 491

(51) Int. Cl.
*H04J 1/04*    (2006.01)
*A61B 5/055*    (2006.01)
(Continued)

(52) U.S. Cl.
CPC .......... *A61B 5/055* (2013.01); *G01R 33/3621* (2013.01)

(58) Field of Classification Search
CPC ............... G01R 33/3621; G01R 33/36; G01R 33/3642; G01R 33/3664; G01R 33/3678; A61B 5/055
See application file for complete search history.

(56) References Cited

U.S. PATENT DOCUMENTS 7,098,659 B2    8/2006    Reykowski et al.
2006/0103386 A1*    5/2006    Buchwald .......... G01R 33/3621
                                                                             324/322

(Continued)

FOREIGN PATENT DOCUMENTS

CN        1532558 A      9/2004
CN    101750592 A      6/2010
(Continued)

OTHER PUBLICATIONS

Chinese Office Action for related Chinese Application No. 201510005163.3 dated May 27, 2017 with English Translation.
(Continued)

*Primary Examiner* — Rishi Patel
(74) *Attorney, Agent, or Firm* — Lempia Summerfield Katz LLC

(57) ABSTRACT

A magnetic resonance imaging apparatus is provided. The apparatus includes a plurality of receiving antennas for receiving a plurality of reception signals. The apparatus also includes at least one first superposition device having at least one first and one second output, which in each case serve for providing a mode formed by superposition of at least two of the reception signals. The apparatus also includes at least one first frequency division multiplex device for transmitting input signal present at a first and a second input of the frequency division multiplex device via a first transmission link on different frequency bands to a receiving unit, wherein the first output of the first superposition device is connected to the first input of the first frequency division multiplex device and the second output of the first superposition device is connected directly or indirectly to a second transmission link.

14 Claims, 4 Drawing Sheets

(51) Int. Cl.
*H04J 1/16* (2006.01)
*G01R 33/36* (2006.01)

(56) References Cited

U.S. PATENT DOCUMENTS

| | | | |
|---|---|---|---|
| 2009/0230966 A1* | 9/2009 | Ehnholm | G01R 33/3415 324/322 |
| 2009/0286478 A1 | 11/2009 | Biber et al. | |
| 2010/0148778 A1 | 6/2010 | Biber | |
| 2010/0201365 A1 | 8/2010 | Bollenbeck | |
| 2010/0225317 A1 | 9/2010 | Biber | |
| 2013/0241547 A1* | 9/2013 | Biber | G01R 33/3692 324/307 |
| 2014/0002087 A1* | 1/2014 | Oppelt | G01R 33/28 324/322 |
| 2014/0002098 A1 | 1/2014 | Sales Casals et al. | |
| 2015/0070014 A1 | 3/2015 | Biber et al. | |
| 2015/0091574 A1* | 4/2015 | Campagna | G01R 33/36 324/318 |

FOREIGN PATENT DOCUMENTS

| | | |
|---|---|---|
| CN | 101806873 A | 8/2010 |
| CN | 103516393 A | 1/2014 |
| DE | 102008023467 A1 | 12/2009 |
| DE | 102008063460 A1 | 7/2010 |
| DE | 102009012109 A1 | 9/2010 |
| DE | 102013218226 A1 | 3/2015 |

OTHER PUBLICATIONS

German Office Action dated Oct. 24, 2014 for corresponding German Patent Application No. DE 10 2014 203 491.4 with English translation.

A. Reykowski, Ph.D, "Tim Matrix Modes," Reprinted from Magnetom Flash, Jan. 2005, No. 30, http://www.siemens.com/magnetom.world, pp. 80-85, 2005.

* cited by examiner

MAGNETIC RESONANCE IMAGING APPARATUS AND METHOD FOR MEASUREMENT SIGNAL ACQUISITION IN A MAGNETIC RESONANCE IMAGING APPARATUS

CROSS-REFERENCE TO RELATED APPLICATIONS

This application claims the benefit of DE 10 2014 203 491.4, filed on Feb. 26, 2014, which is hereby incorporated by reference in its entirety.

TECHNICAL FIELD

The embodiments relate to a magnetic resonance imaging apparatus including a plurality of receiving antennas for receiving a plurality of reception signals, at least one first superposition device having at least one first and one second output, which in each case serve for providing a mode formed by superposition of at least two of the reception signals, and at least one first frequency division multiplex device for transmitting input signals present at one first and one second input of the frequency division multiplex device via a first transmission link on different frequency bands to a receiving unit.

BACKGROUND

A multiplicity of local coils including one or more receiving antennas for magnetic resonance signals may be used in magnetic resonance imaging apparatuses. Owing to the dictates of the structural design and in particular for cost reasons, it is possible that an assigned receiving unit may not simultaneously acquire the signals of all the receiving antennas. It is possible, in particular, that the same receiving antenna configuration is intended to be usable with different receiving units having a different number of channels.

The limiting factors when guiding reception signals from the receiving antenna to a processing unit in this case include the number of transmission links, e.g., the number of signal lines present, and the receiving possibilities of the receiving unit, such as the number of analog-to-digital conversion channels present or the number of further processing stages of the receiving unit.

It is known to use so-called mode matrices in order to superpose the reception signals of a plurality of receiving antennas in a complexly weighted fashion, e.g., with a respective amplitude and a respective phase offset. In this case, the signals of a plurality of receiving antennas are superposed such that a so-called primary or CP mode in the center of the examination region has a particularly high signal-to-noise ratio. In addition, higher modes are formed, (for example, the so-called secondary mode and/or tertiary mode), which map the edge regions of the examination region particularly well. If, by way of example, a single receiving channel is intended to be used for the group of receiving antennas fed into such a mode matrix, then exclusively the primary mode may be acquired. In this case, the reception signals may be superposed in the mode matrix in such a way that the number of output signals provided is exactly the same as the number of reception signals fed in, wherein the reception signals may be completely reconstructed during the evaluation of all the output signals.

In order to reduce the number of required transmission channels, it is known, moreover, to combine the different modes of a mode matrix to form a common transmission signal by the use of a frequency division multiplexer. What is disadvantageous in this case is that a separate transmission link and a separate input at the receiving unit have to be provided for each of the mode matrices used.

SUMMARY AND DESCRIPTION

The scope of the present invention is defined solely by the appended claims and is not affected to any degree by the statements within this summary. The present embodiments may obviate one or more of the drawbacks or limitations in the related art.

The embodiments are based on specifying a magnetic resonance imaging apparatus that is improved by comparison therewith, in particular, with regard to the scalability of the number of inputs of the receiving unit.

A magnetic resonance imaging apparatus is provided, wherein the first output of the first superposition device is connected to the first input of the first frequency division multiplex device and the second output of the first superposition device is connected directly or indirectly to a second transmission link.

A superposition device, also called mode matrix, is proposed in conjunction with at least one frequency division multiplexer, but distributing the different modes of the superposition device among different transmission links. The modes generated by the superposition device may have a different significance. For example, the acquisition of some of the modes may be dispensed with in cases in which only a small number of receiving channels are available. By dividing the modes of a superposition device among different transmission links in the manner, what is achieved is that not all the transmission links have to be led to inputs of the receiving unit. Therefore, it is possible, for example, to use complex local coils having a multiplicity of receiving antennas even in magnetic resonance imaging apparatuses that provide only a relatively small number of transmission links to the receiving unit. In addition, with use of fewer modes, the number of inputs of the receiving unit may also be reduced. The magnetic resonance imaging apparatus therefore combines the scaling advantages of using different modes with the advantages of a reduced number of required transmission links by the use of frequency division multiplex devices.

A connection to a transmission link may in this case correspond to a connection of a cable in the case where a cable-based transmission is used. If a radio-based transmission is used, then the transmission links are frequency bands of a radio connection. A connection to the corresponding transmission link corresponds to a communication on this frequency band. In this case, the second output of the first transmission device may be connected to the second transmission link directly, e.g., without further processing of the signal. Alternatively, it is also possible, however, for the mode provided at the second output of the superposition device to be fed to further processing devices, in particular a further frequency division multiplex device, and for the signal that has been processed further to be fed to the second transmission link.

The superposition device may output at the first output in particular a primary or CP mode that, in a central region of the examination volume of the coils fed to the superposition device, has a higher signal-to-noise ratio than the further modes provided. The number of outputs of the superposition device is, in particular, equal to the number of reception signals fed to the superposition device. Alternatively, it would be possible to use a superposition device having a smaller number of outputs. In this case, the modes of higher significance that map central examination regions particularly well may still be transmitted, but modes of low significance may be terminated or not generated.

An arbitrary number of receiving antennas, superposition devices, and frequency division multiplex devices may be used in the magnetic resonance imaging apparatus. In particular, it is possible for the output signals of each of the superposition devices to be fed to at least two different transmission links directly or via additional frequency division multiplex devices.

The receiving unit may receive and process the signals transmitted via the transmission links in diverse ways. At least those signals that are fed to a transmission link via a frequency division multiplex device have already been converted to an intermediate frequency. In order to enable easier digitization of the signals, it is possible to choose intermediate frequencies that are below the received Larmor frequencies. It is possible to use converters having a lower conversion rate or time division multiplexing is possible for the converters. It is also possible to provide generation of intermediate frequencies also for reception signals that are not passed via a frequency division multiplex device. Conversion to an intermediate frequency may be carried out as early as within a local coil including one or more receiving antennas, or not until in the receiving unit itself. In addition, it is also possible for signals first to be transmitted on a first intermediate frequency and to be converted to a second intermediate frequency in the receiving unit. Alternatively or additionally, direct analog-to-digital conversion of the signals transmitted via the transmission links without preceding conversion to an intermediate frequency is also possible.

It is possible, in particular, that the receiving unit directly converts signals transmitted by a frequency division multiplex device, and the signals combined by the frequency division multiplex device are separated only in the context of the further processing of the digital data.

The magnetic resonance imaging apparatus may include at least one second superposition device and/or at least one second frequency division multiplex device. Three or more superposition devices and/or frequency division multiplex devices may also be provided. The second output of the first superposition device may be connected in particular to an input of the second frequency division multiplex device. Alternatively or additionally, a first output of the second superposition device may be connected to a second input of the first frequency division multiplex device. In this regard, it is possible, for example, for the first and second superposition devices in each case to provide a primary mode and a secondary mode and for both primary modes to be fed to the first frequency division multiplex device and both secondary modes to be fed to the second frequency division multiplex device. Both primary modes may be received even with use of exclusively one transmission link and thus only one input of the receiving unit.

It is possible for more than two modes of identical significance to be fed to a frequency division multiplex device and transmitted via a common transmission link. Alternatively or additionally, it is also possible to use superposition devices that provide three or more modes of different significance, which then in each case are fed to different frequency division multiplex devices separately according to the significance of the mode and are transmitted via separate transmission links.

In particular, the first superposition device and the second superposition device may have in each case the same number of outputs and at least three outputs, wherein the respective outputs serve for providing modes of different significance with different signal-to-noise ratios in a central region of the examination volume. It is possible that respective inputs of the first frequency division multiplex device and/or of the second frequency division multiplex device are connected to an output of the first superposition device and an output of the second superposition device to which modes of identical significance are assigned. Alternatively or additionally, it is possible that the second output of the first superposition device is directly connected to the second transmission link and an output of the second superposition device is directly connected to a third transmission link, wherein modes of different significance are assigned to the second output of the first superposition device and the output of the second superposition device. As also explained below with respect to specific exemplary embodiments, a particularly efficient utilization of receiving channels may be achieved by the transmission of modes of identical significance via a common frequency division multiplex device or by a separate transmission of different modes of different superposition devices.

The first frequency division multiplex device may have exactly two inputs. In particular, all the frequency division multiplex devices used in the magnetic resonance imaging apparatus may have exactly two inputs. In this case, firstly, the signals may be combined particularly easily by a diplex filter after the frequency conversion of the input signals to two different frequencies. Secondly, the intermediate frequencies may be chosen symmetrically to a conversion rate of an analog-to-digital converter, as a result of which signals of identical frequency are present after separation of the signals by a filter and conversion of both signals, which facilitates a further processing.

In addition, the embodiments relate to a method for measurement signal acquisition in a magnetic resonance imaging apparatus, the method including:
(1) superposing the reception signals of a plurality of receiving antennas by a superposition device to form at least one first and one second mode, which are provided at a respective output, (2) feeding the first mode to a first transmission link via a frequency division multiplex device, (3) directly or indirectly feeding the second mode to a second transmission link, and (4) receiving the first and the second mode from the respective transmission link by a receiving unit.

The method may be developed, of course, in accordance with the magnetic resonance imaging apparatus.

DETAILED DESCRIPTION

FIGS. 1 to 5 schematically depict different exemplary embodiments of a magnetic resonance imaging apparatus in which both superposition devices and frequency division multiplex devices are used for signal transmission from the receiving antennas to the receiving unit. The structure of a corresponding magnetic resonance imaging apparatus is firstly explained with reference to FIG. 1. The subsequent FIGS. 2 to 5 depict particularly advantageous exemplary embodiments of the magnetic resonance imaging apparatus.

Figure 1:
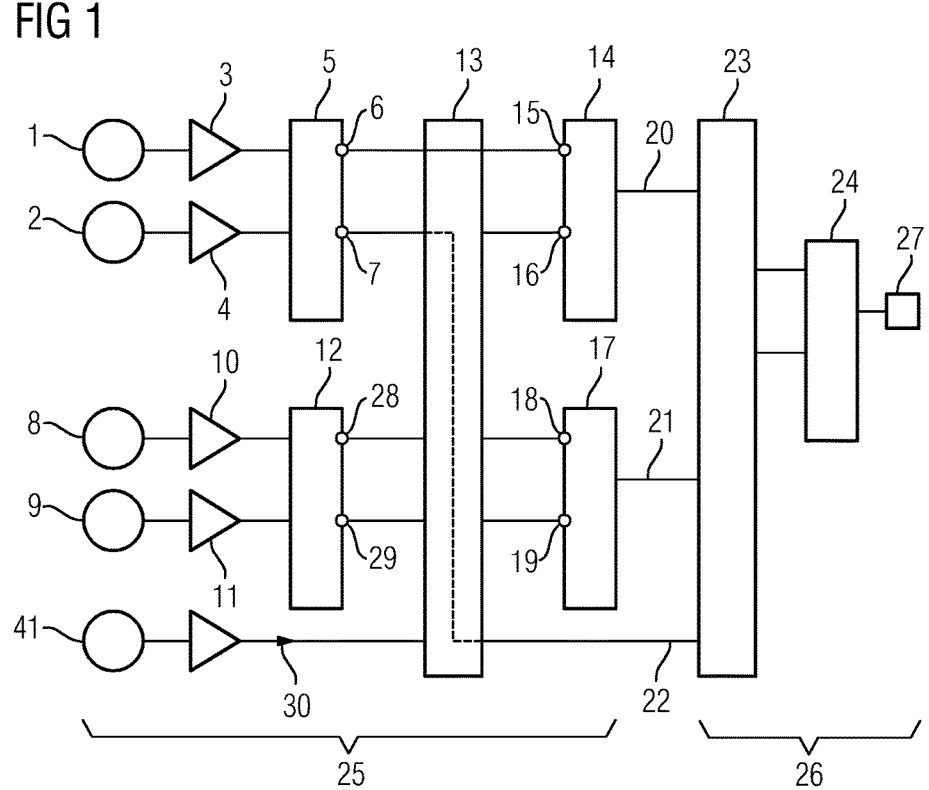
FIG. 1 schematically depicts one exemplary embodiment of a magnetic resonance imaging apparatus.

In FIG. 1, the two receiving antennas 1 and 2 are fed respectively to a linear amplifier 3 and 4. The linear amplifier 3, 4 decouples the reception of the reception signals at the receiving antennas 1, 2 from the subsequent further processing. The reception signals are fed to a superposition device 5 after the prior amplification. The superposition device 5, also called mode matrix, superposes the reception signals received by the receiving antennas 1 and 2, wherein each of the signals is weighted with a complex prefactor. This provides that both the amplitude of the signals and the phase of the signals are configured for the superposition of the signals.

The modes provided at the first output 6 and at the second output 7 of the superposition device 5 differ from the signals of the individual receiving antennas 1, 2 with regard to the distribution of their sensitivity in the examination volume. In this case, a primary mode, also called CP mode, is output at the first output 6, the mode corresponding to a circularly polarized superposition of the signals of the receiving antennas 1, 2. In this case, the primary mode has the property of having a particularly high signal-to-noise ratio in the central region of the examination volume of the receiving antennas 1, 2. By contrast, the mode output at the second output 7 has a higher signal-to-noise ratio in the edge region of the examination volume than in the central region.

The superposition device 5 and the superposition devices described below are designed in such a way that the number of input signals is equal to the number of outputs 6, 7 and thus equal to the number of modes formed. In this case, the modes are formed in such a way that the original reception signals may be recovered during the evaluation of all the modes.

The modes provided at the outputs 6, 7 of the superposition device 5 are allocated a significance, wherein modes that map in particular the central region of an examination volume with a high signal-to-noise ratio, (e.g., the primary mode), are designated as of higher significance. During the plurality of magnetic resonance examinations, a high signal-to-noise ratio in this central examination region is relevant, in particular. Therefore, the acquisition of the modes of lower significance may often be dispensed with, in conjunction with only low losses of measurement quality. The use of the superposition device 5 therefore permits, in particular, a better scaling of the receiving channels of the receiving unit, since only the modes of higher significance may be received in the case of a small number of receiving channels.

In an alternative embodiment, it is possible to use a superposition device 5 that may superpose more than two input signals to form more than two modes. Signals of further receiving antennas may accordingly be acquired.

The receiving antennas 8, 9 are fed via the linear amplifiers 10, 11 to a second superposition device 12, which likewise provides at its outputs 28, 29 a primary and a secondary mode formed by superposition of the signals of the receiving antennas 8, 9. Outside the superposition devices 5, 12, in an alternative embodiment of the magnetic resonance imaging apparatus, further superposition devices may also be provided, to which reception signals of further receiving antennas are fed. In this case, the further processing of the signals would be effected in accordance with the further processing explained below of the signals at the outputs 6, 7, 28, 29 of the superposition devices 5, 12.

The signals provided by the outputs 6, 7, 28, 29 and also a further reception signal 30, which was received by a further receiving antenna 41, are fed to the redistribution wiring block 13. The redistribution wiring block 13 is depicted as a separate functional unit in FIG. 1, but constitutes exclusively the wiring between the outputs 6, 7, 28, 29 of the superposition devices 5, 12 and respectively the further receiving antenna 41 and the inputs 15, 16, 18, 19 of the frequency division multiplex devices 14, 17 and respectively a transmission link 22. The wiring in the redistribution wiring block 13 may be fixedly predefined for a given magnetic resonance imaging apparatus or for a local coil 25 in a magnetic resonance imaging apparatus that includes alongside the receiving antennas 1, 2, 8, 9 linear amplifiers 3, 4, 10, 11, the superposition devices 5, 12 and the frequency division multiplex devices 14, 17. In an alternative embodiment, however, it would also be possible to provide a switchable wiring as redistribution wiring block 13 in order to enable different signal routings.

A feature of the redistribution wiring block 13 is that by the wiring the first output 6 of the superposition device 5 is fed to the first input 15 of the first frequency division multiplex device 14 and via the latter to a first transmission link 20 and the second output 7 of the first superposition device 5 is fed to a second transmission link 22. The feed to the second transmission link 22 is depicted in a dashed manner since, in an alternative embodiment, the transmission link 21 may also be provided as second transmission link. In such an embodiment, the second output 7 of the first superposition device 5 may be fed to the first input 18 or to the second input 19 of the second frequency division multiplex device 17. The routing of the signals from the outputs 28, 29 and of the further reception signal 30 is not depicted for the sake of improved clarity, an arbitrary redistribution among the remaining outputs of the redistribution wiring block 13 being possible.

The first frequency division multiplex device 14 converts the signals fed to the inputs 15, 16 to two different intermediate frequencies by a respective mixer, combines the signals and transmits them via the first transmission link 20 to a signal selection unit 23. The latter selects that input signals are subsequently fed to the converter unit 24. The intermediate frequencies are chosen in such a way that they lie symmetrically above and below a sampling rate of a converter of the converter unit 24. If the signals in the converter unit 24 are separated again by a high-pass filter and respectively low-pass filter and subsequently converted. The signals therefore, since they lie in different aliasing bands, fall into the same frequency range, which facilitates further processing. The converter unit 24 and the signal selection unit 23 jointly form the receiving unit 26.

In an alternative embodiment of the magnetic resonance imaging apparatus, the frequency division multiplex device 14 may also have additional inputs, wherein in this case the signals at the different inputs are respectively mixed to different intermediate frequencies.

The processing of the signals at the inputs 18, 19 of the second frequency division multiplex device 17 to form a common signal that is transmitted via the transmission link 21 is effected as described with regard to the first frequency division multiplex device 14. Alongside the first and second frequency division multiplex devices 14, 17, in an alternative embodiment of the magnetic resonance imaging apparatus, further frequency division multiplex devices may also be provided in order to combine further input signals and to transmit them on further transmission links.

The data received by the receiving unit 26 are provided via a digital bus to the further components 27 of the magnetic resonance imaging apparatus. In this case, the further components 27 serve for data processing and evaluation and provision of magnetic fields for the measurements by the magnetic resonance imaging apparatus. The corresponding components are known in the prior art and shall not be explained in further detail here.

Figure 2:
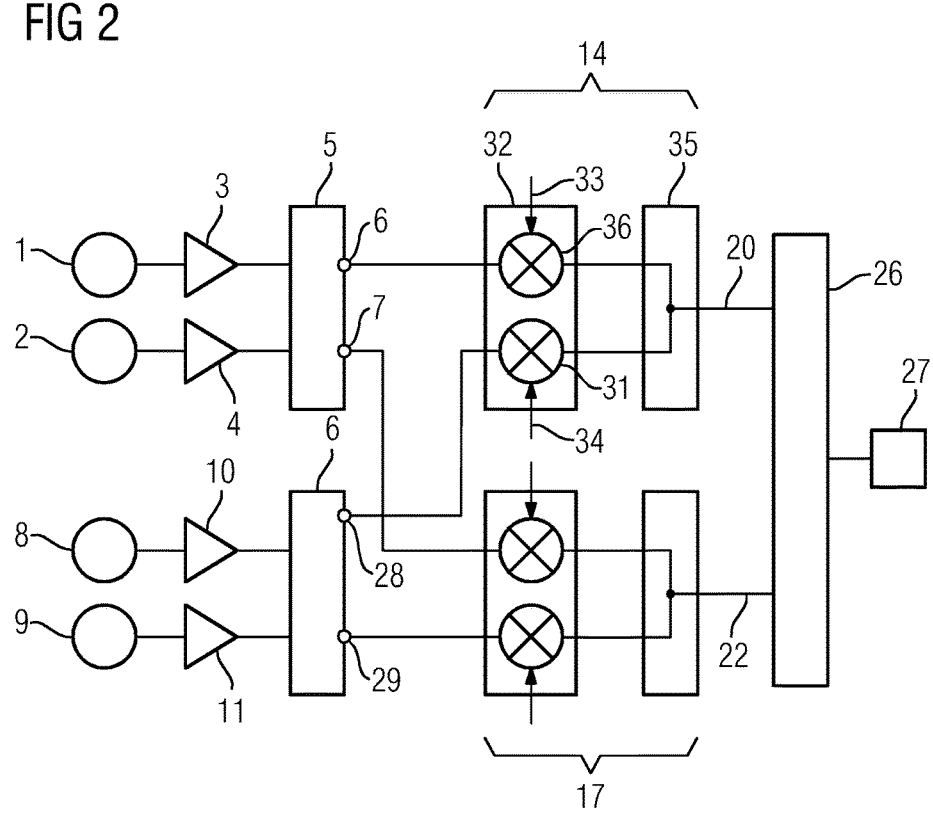
FIG. 2 schematically depicts a further exemplary embodiment of a magnetic resonance imaging apparatus.

FIG. 2 depicts a further exemplary embodiment of a magnetic resonance imaging apparatus. In this exemplary embodiment and also the subsequent exemplary embodiments described with reference to FIGS. 3, 4 and 5, the basic construction of the magnetic resonance imaging apparatus corresponds, in principle, to the construction explained with regard to FIG. 1. Therefore, only the specific features of the individual exemplary embodiments are discussed below.

The exemplary embodiment in accordance with FIG. 2 has a different signal routing between the first and second superposition devices 5, 6 and the first and second frequency division multiplex devices 14, 17 than the magnetic resonance imaging apparatus depicted in FIG. 1. In this case, the first output 6 of the first superposition device 5 and the first output 28 of the second superposition device 6 are fed to the first frequency division multiplex device 14 and the second output 7 of the first superposition device 5 and the second output 29 of the second superposition device 6 are fed to the second frequency division multiplex device 17. Since the superposition devices 5, 6 in each case provide the primary mode at their first outputs 6, 28 and the secondary mode at their second outputs 7, 29, the two primary modes are transmitted on the first transmission link 20 and the two secondary modes are transmitted on the second transmission link 22. This is advantageous, in particular, if only one signal of a transmission link may or is intended to be processed by the receiving unit 26. In this case, exclusively the signal of the first transmission link 20 may be evaluated, as a result of which both primary modes are available.

FIG. 2 additionally depicts the construction of the first and second frequency division multiplex devices 14, 17 in detail. In this case, the first frequency division multiplex device 14 includes a mixer device 32, which with the mixer 36 multiplies a first input signal by a first fed signal 33. A second input signal is correspondingly multiplied by a second fed signal 34 by the mixer 31. The multiplication of a signal by a second signal results in the formation of two sidebands in the frequency spectrum. In the frequency division multiplex device 14, both intermediate frequencies are intended to be lower than the original signal frequency, for which reason a low-pass filter is connected downstream of the mixers 31, 36. The signals are subsequently combined by a diplex filter 35, which feeds one of its inputs via a high-pass filter and one of its inputs via a low-pass filter to the transmission link 20. The construction of the second frequency division multiplex device 17 likewise corresponds to the construction explained.

Figure 3:
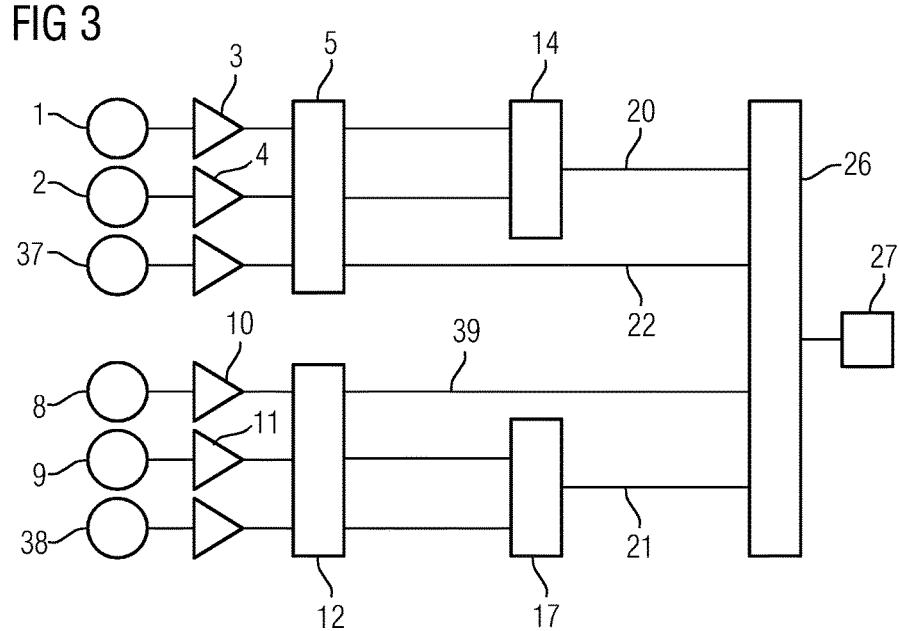
FIG. 3 schematically depicts a third exemplary embodiment of a magnetic resonance imaging apparatus.

FIG. 3 depicts a third exemplary embodiment of a magnetic resonance imaging apparatus. In contrast to the previous exemplary embodiments, the first and second superposition devices 5, 12 have three inputs and also provide three modes at their outputs. In this case, the reception signal of the further receiving antenna 37 and respectively of the further receiving antenna 38 is fed to the third input. The primary and secondary modes of the first superposition device 5 are fed via the first frequency division multiplex device 14 jointly to the first transmission link 20. The tertiary mode is fed separately and without further frequency conversion directly to the second transmission link 22. The primary mode of the second superposition device 12 is fed separately and without frequency conversion directly to the transmission link 39. The secondary and tertiary modes are combined by the frequency division multiplex device 17 and jointly transmitted via the transmission link 21.

In the case of receiving units 26 of magnetic resonance imaging apparatuses, receiving channels may be provided for receiving signals of a frequency division multiplex device and receiving channels may be provided for receiving signals that are transmitted directly at the Larmor frequency without conversion to an intermediate frequency. In this case, the provision of both types of inputs may serve to provide compatibility with types of coils that use frequency conversion and those that do not. The embodiment of the magnetic resonance imaging apparatus depicted in FIG. 3 enables such receiver units 26 to be used particularly efficiently. If exclusively the signals of the receiving antennas 1, 2 and 37 are intended to be used, then the signals on the transmission links 20 and 22 may be evaluated. If the signals of all the receiving antennas 1, 2, 8, 9, 37, 38 are intended to be evaluated, then the signal of the transmission link 20 and the signal of the transmission link 39 may be acquired. Therefore, the primary and secondary modes for the receiving antennas 1, 2 and 37 are available and the primary mode for the receiving antennas 8, 9 and 38. An optimum utilization of the available receiving channels is thus possible.

Figure 4:
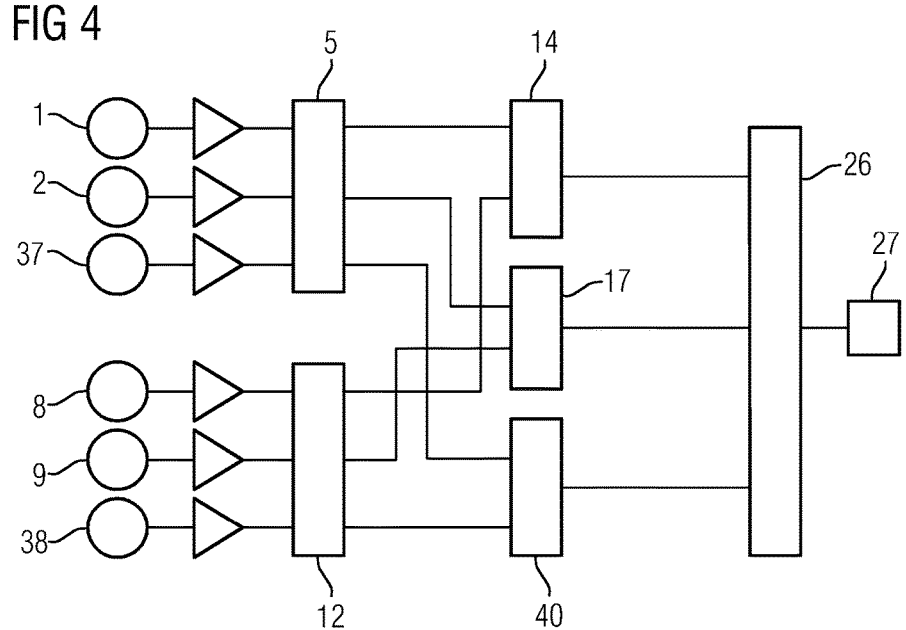
FIG. 4 schematically depicts a fourth exemplary embodiment of a magnetic resonance imaging apparatus.
Figure 5:
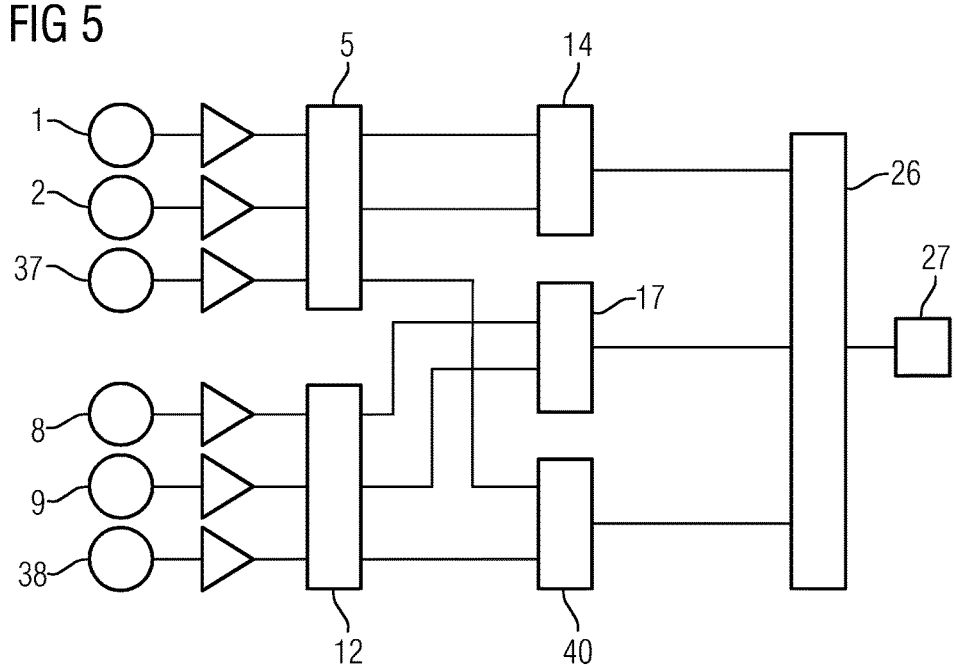
FIG. 5 depicts a fifth exemplary embodiment of a magnetic resonance imaging apparatus.

FIGS. 4 and 5 depict exemplary embodiments of a magnetic resonance imaging apparatus in which, as already in FIG. 3, first and second superposition devices 5, 12 are used which in each case convert three input signals to form three separate modes. In both exemplary embodiments, however, the receiving unit 26 is embodied in such a way that it is possible to receive signals transmitted at intermediate frequencies by the frequency division multiplex devices 14, 17, 40 on all available channels.

In FIG. 4, the primary modes of the first and second superposition devices 5, 12 are in each case fed to the frequency division multiplex device 14, the secondary modes are fed to the frequency division multiplex device 17, and the tertiary modes are fed to the frequency division multiplex device 40. What is achieved by a respective combination of the primary, secondary, and tertiary modes on a separate transmission link is that if only one input channel is available at the receiving unit 26, all primary modes are available, and given an availability of two input channels all primary and secondary modes are available, and given an availability of three input channels all modes are available.

FIG. 5 depicts a variant of the exemplary embodiment in FIG. 4, in which both tertiary modes of the first and second superposition devices 5, 12 are still fed to a common frequency division multiplex device 40. However, the primary and secondary modes of the superposition device 5 are both fed to the frequency division multiplex device 14 and the primary and secondary modes of the superposition device 12 are both fed to the frequency division multiplex device 17. Such an interconnection is advantageous if it may be assumed that at least two receiving channels for the signals of the receiving antennas 1, 2, 8, 9, 37 and 38 are always available at the receiving unit 26. The primary and secondary modes are always available in this case. If a third receiving channel is additionally available, the tertiary mode may also be acquired.

In the case of the wiring depicted in FIG. 5, it is possible under certain circumstances to simplify in particular the construction of the magnetic resonance imaging apparatus in comparison with the wiring depicted in FIG. 4, since the functions of the superposition device 5 and of the frequency division multiplex device 14 and respectively of the superposition device 12 and of the frequency division multiplex device 17 may be embodied as common switching groups.

Figure 6:
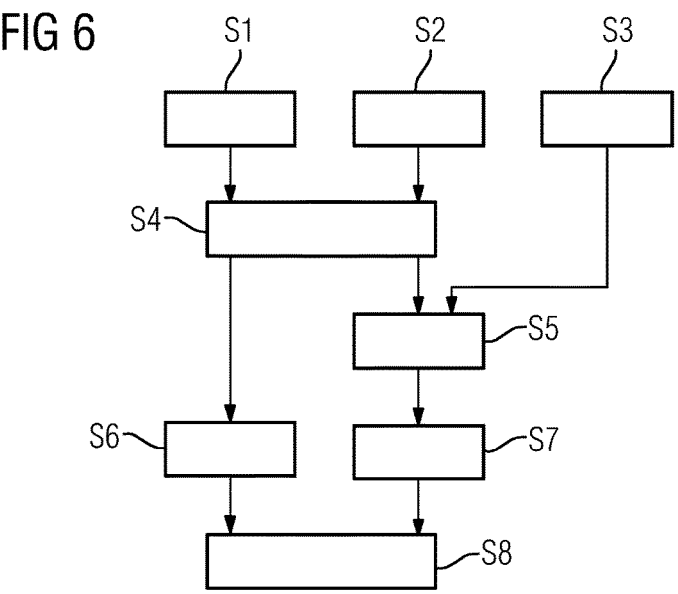
FIG. 6 schematically depicts a flowchart of one exemplary embodiment of a method.

FIG. 6 depicts a flowchart of one exemplary embodiment of a method for measurement signal acquisition in a magnetic resonance imaging apparatus. In this case, in act S1 a first reception signal is received by a first receiving antenna and, in act S2, a second reception signal is received by a second receiving antenna. In act S3, in addition a third signal is provided, which may be for example the reception signal of a third receiving antenna or a mode signal provided by a superposition device. In act S4, the reception signals received in act S1 and act S2 are superposed by a superposition device. As a result, as explained with reference to FIG. 1, a primary and a secondary mode are provided at a first and a second output of the superposition device. In act S5, the further signal provided in act S3 is combined with the signal provided at the first output of the superposition device in act S4 by a frequency division multiplex device. For this purpose, both signals are converted by a mixer and, under certain circumstances, downstream filtering in each case to different intermediate frequencies and the signals thus present are combined in different frequency bands. One possible procedure for this signal combination is described with reference to FIG. 2.

In act S6, the signal provided at the second output of the superposition device in act S4 is transmitted to a receiving unit. In this case, the transmission takes place directly, e.g., no frequency conversion takes place. Alternatively, in an additional act, frequency conversion of the signal may be provided, in particular for frequency division multiplexing with a further signal.

In parallel therewith, in act S7, the superposed signal provided by the frequency division multiplex device in act S5 is transmitted to the receiving unit.

In act S8, the receiving unit receives the signals provided, extracts the measurement information and makes the latter available for further processing.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance imaging apparatus comprising:
a plurality of receiving antennas for receiving a plurality of reception signals;
a first superposition device comprising a first output and a second output, the first output and the second output each providing a mode formed by superposition of at least two of the reception signals; and
a local coil comprising a first frequency division multiplex device and a second frequency division multiplex device, the first frequency division multiplex device for transmitting an input signal present at a first input and an input signal present at a second input of the first frequency division multiplex device via a first transmission link on different frequency bands to a receiving unit,
wherein the first output of the first superposition device is connected to the first input of the first frequency division multiplex device and the second output of the first superposition device is in signal connection with a second transmission link, and
wherein the second output of the first superposition device is also connected to an input of the second frequency division multiplex device of the local coil.

2. The magnetic resonance imaging apparatus as claimed in claim 1, further comprising a second superposition device.

3. The magnetic resonance imaging apparatus as claimed in claim 2, wherein the first superposition device and the second superposition device each have a same number of outputs and each have at least three outputs, wherein the respective outputs serve for providing modes of different significance with different signal-to-noise ratios in a central region of an examination volume.

4. The magnetic resonance imaging apparatus as claimed in claim 3, wherein respective inputs of the first frequency division multiplex device, the second frequency division multiplex device, or both the first and the second frequency division multiplex devices are connected to an output of the first superposition device and an output of the second superposition device to which modes of identical significance are assigned.

5. The magnetic resonance imaging apparatus as claimed in claim 4, wherein the second output of the first superposition device is directly connected to the second transmission link and an output of the second superposition device is directly connected to a third transmission link,
wherein modes of different significance are assigned to the second output of the first superposition device and the output of the second superposition device.

6. The magnetic resonance imaging apparatus as claimed in claim 3, wherein the second output of the first superposition device is directly connected to the second transmission link and an output of the second superposition device is directly connected to a third transmission link,
wherein modes of different significance are assigned to the second output of the first superposition device and the output of the second superposition device.

7. The magnetic resonance imaging apparatus as claimed in claim 1, wherein the first frequency division multiplex device comprises exactly two inputs.

8. A magnetic resonance imaging apparatus comprising:
a plurality of receiving antennas for receiving a plurality of reception signals;
a first superposition device comprising a first output and a second output, the first output and the second output each providing a mode formed by superposition of at least two of the reception signals;
a first frequency division multiplex device for transmitting an input signal present at a first input and an input signal present at a second input of the first frequency division multiplex device via a first transmission link on different frequency bands to a receiving unit; and a second superposition device,
wherein the first output of the first superposition device is connected to the first input of the first frequency division multiplex device and the second output of the first superposition device is connected directly or indirectly to a second transmission link, and
wherein a first output of the second superposition device is connected to a second input of the first frequency division multiplex device.

9. The magnetic resonance apparatus as claimed in claim 8, further comprising:
a second frequency division multiplex device,
wherein the second output of the first superposition device is connected to an input of the second frequency division multiplex device.

10. The magnetic resonance imaging apparatus as claimed in claim 9, wherein the first superposition device and the second superposition device each have a same number of outputs and each have at least three outputs, wherein the respective outputs serve for providing modes of different significance with different signal-to-noise ratios in a central region of an examination volume.

11. The magnetic resonance imaging apparatus as claimed in claim 10, wherein respective inputs of the first frequency division multiplex device, the second frequency division multiplex device, or both the first and the second frequency division multiplex devices are connected to an output of the first superposition device and an output of the second superposition device to which modes of identical significance are assigned.

12. The magnetic resonance imaging apparatus as claimed in claim 11, wherein the second output of the first superposition device is directly connected to the second transmission link and an output of the second superposition device is directly connected to a third transmission link,
wherein modes of different significance are assigned to the second output of the first superposition device and the output of the second superposition device.

13. The magnetic resonance imaging apparatus as claimed in claim 12, wherein the first frequency division multiplex device comprises exactly two inputs.

14. The magnetic resonance imaging apparatus as claimed in claim 10, wherein the second output of the first superposition device is directly connected to the second transmission link and an output of the second superposition device is directly connected to a third transmission link,
wherein modes of different significance are assigned to the second output of the first superposition device and the output of the second superposition device.

* * * * *